US012364660B2

(12) United States Patent
Sitterberg-Muehlthau et al.

(10) Patent No.: US 12,364,660 B2
(45) Date of Patent: Jul. 22, 2025

(54) GRANULATED HAIR DYE COMPOSITION

(71) Applicants: WELLA GERMANY GMBH, Darmstadt (DE); Wella International Operations Switzerland SARL, Petit Lancy (CH)

(72) Inventors: Stephanie Sitterberg-Muehlthau, Kelkheim (DE); David Sarro, Frankfurt am Main (DE); Dominik Hess, Darmstadt (DE); Franziska Eekhoff, Solingen (DE)

(73) Assignees: WELLA GERMANY GMBH, Darmstadt (DE); Wella International Operations Switzerland, Petit Lancy (CH)

( * ) Notice: Subject to any disclaimer, the term of this patent is extended or adjusted under 35 U.S.C. 154(b) by 0 days.

(21) Appl. No.: 18/253,771

(22) PCT Filed: Nov. 19, 2021

(86) PCT No.: PCT/EP2021/082321
§ 371 (c)(1),
(2) Date: May 19, 2023

(87) PCT Pub. No.: WO2022/106628
PCT Pub. Date: May 27, 2022

(65) Prior Publication Data
US 2023/0414484 A1 Dec. 28, 2023

Related U.S. Application Data

(60) Provisional application No. 63/116,244, filed on Nov. 20, 2020.

(51) Int. Cl.
*A61Q 5/10* (2006.01)
*A61K 8/02* (2006.01)
*A61K 8/73* (2006.01)
*A61K 8/9783* (2017.01)
*A61Q 5/06* (2006.01)

(52) U.S. Cl.
CPC .......... *A61K 8/9783* (2017.08); *A61K 8/0225* (2013.01); *A61K 8/737* (2013.01); *A61Q 5/065* (2013.01); *A61K 2800/4322* (2013.01)

(58) Field of Classification Search
CPC .... A61K 8/9783; A61K 8/0225; A61K 8/737; A61K 2800/4322; A61K 8/492; A61K 8/73; A61Q 5/065
USPC .......................................................... 8/405
See application file for complete search history.

(56) References Cited

U.S. PATENT DOCUMENTS 6,302,920 B1    10/2001    Lorenz et al.

FOREIGN PATENT DOCUMENTS

| DE | 4219181 A1 | 2/1994 | |
| EP | 0572768 A2 * | 12/1993 | ............... A61Q 5/10 |
| EP | 0806199 A2 | 11/1997 | |
| EP | 0806200 A2 | 11/1997 | |
| EP | 3431071 A1 * | 1/2019 | ............... A61Q 5/08 |
| WO | WO 9725017 A1 * | 7/1997 | ............... A61Q 5/10 |
| WO | 2013083701 A1 | 6/2013 | |
| WO | 2013083702 A1 | 6/2013 | |
| WO | 2014174113 A2 | 10/2014 | |

OTHER PUBLICATIONS

International Search Report in connection with PCT/EP2021/082321 issued on Mar. 21, 2022.
International Written Opinion in connection with PCT/EP2021/082321 issued on Mar. 21, 2022.
Response to Written Opinion in connection with PCT/EP2021/082321 Filed on Nov. 16, 2022.
International Preliminary Report on Patentability in connection with PCT/EP2021/082321 issued on Feb. 17, 2023.

* cited by examiner

*Primary Examiner* — Eisa B Elhilo
(74) *Attorney, Agent, or Firm* — Dennemeyer & Associates LLC

(57) ABSTRACT

It is provided a granulated hair dye composition, a poultice obtained with it, a method for preparing it and a method for dyeing thereof. The granulated hair dye composition comprises a natural hair dyeing agent, a natural thickening agent, and optionally a direct dye, wherein the natural dyeing agent is coated with the natural thickening agent, thereby forming granules. It is provided a dust-free composition, comprising fewer materials than conventional non-oxidative hair dyeing compositions, and mostly from natural origin, that could be easily mixed with water and applied onto hair as a poultice with limited or no dripping, while providing an improved user's dyeing experience and an even dyeing of hair, without comprising shine and hair feel.

12 Claims, No Drawings

GRANULATED HAIR DYE COMPOSITION

CROSS-REFERENCE TO RELATED APPLICATIONS

This is a 35 U.S.C. 371 National Stage Patent Application of International Application No. PCT/EP2021/082321, filed Nov. 19, 2021, which claims priority to U.S. Provisional Application No. 63/116,244, filed Nov. 20, 2020, each of which is hereby incorporated by reference in its entirety.

TECHNICAL FIELD

The present invention relates to a granulated hair dye composition, a method for preparing it and a method of use thereof. The granulated hair dye composition comprises a natural hair dyeing agent, a natural thickening agent, and optionally a direct dye, wherein the natural dyeing agent are coated with the natural thickening agent, thereby forming granules. The present invention provides a dust-free composition, comprising fewer materials than conventional non-oxidative hair dyeing compositions, and mostly from natural origin, that could be easily mixed with water and applied onto hair as a poultice with limited or no dripping, while providing an improved user's dyeing experience and an even dyeing of hair, plus providing exceptional shine and significantly improved hair feel.

BACKGROUND

Hair is customarily dyed using an oxidative hair dyeing method or a non-oxidative hair dyeing method.

Oxidative hair dyeing is achieved by using an oxidative hair dyeing composition comprising at least oxidative dyes (including primary intermediates and couplers), an oxidizing agent and an alkalizing agent. Oxidative hair dyeing methods provide a long-lasting (permanent) dyeing of hair, a good wash fastness and a great variety of shades. However, such methods are cumbersome and may damage hair and cause allergic reactions or skin intolerances.

Non-oxidative hair dyeing is achieved by using non-oxidative hair dyeing compositions comprising natural dyes and/or direct dyes, while being usually free of any oxidizing agent and/or alkalizing agent. Non-oxidative hair dyeing methods only provide a semi-permanent dyeing of hair, while causing no to limited damages and no to limited allergic reactions or skin intolerances.

Over the past years, the users—consumers and hairdressers—have shown an increasing interest in using non-oxidative hair dyeing methods, instead of oxidative hair dyeing methods. Particularly, the users have developed an ever-increasing interest for "natural and safe" products i.e. for products comprising compounds obtained/derived from natural origin, particularly from plant origin, and being—as much as possible—free of synthetic chemical compounds, particularly those derived from crude oil. There is also an ever-increasing interest for "simple and efficient" products i.e. products comprising fewer compounds, without compromising its efficiency.

Natural dyes, such as henna powders (*Lawsonia Inermis* leaf powder) and powders of indigo-yielding plants (e.g. *Indigofera Tinctoria* leaf powder), have been used for centuries for dyeing keratin fibers, particularly for dyeing hair. Other natural dye powders have also been obtained for example from chamomile flowers, *curcuma* roots, rhubarb, buckthorn bark, olive tree leaves, Canadian bloodroot, turmeric, yellowwood, redwood, logwood, madder root, black elderberry, black chokeberry.

Coarse raw powders are traditionally mixed with water, particularly warm water, before application onto hair as a poultice. However, such coarse raw powders usually comprise granules of various size and the mixing with water, for obtaining a poultice, is uneasy and not homogenous. Fine powders have also been used. However, even though the mixing with water may be facilitated, such fine powders generate lots of dust. In addition, the mixture obtained may be difficult to apply onto hair and to rinse off, may thus still lead to an uneven dyeing of keratin fibers. In addition, these coarse raw powders may exhibit the separation of components of different densities through transport and storage. Hence, the heavier components tend to accumulate at the bottom while the lighter components tend accumulate at the top of the container. The same amount of powder mixture may thus give different compositions and, consequently, different colouring results, which is highly unwanted by the user.

Different formulations have been developed, in an attempt to provide dust-free hair dyeing compositions having a satisfactory dyeing performance. For example, the U.S. Pat. No. 6,302,920 B1 particularly discloses a flowable pulverulent bleaching or dyeing composition, coated or agglomerated by spraying a melted wax compound having a flow point between about 40 and about 130° C. The European patent applications EP 0806199 A1 and EP 0806200 A2 particularly disclose hair dyeing compositions, in the form of suspensions, comprising a powdered natural dyeing agent and an oil. International applications WO 2013/083701 A1 and WO 2013/083702 A1 disclose hair dyeing compositions comprising natural dyes and an oil and/or a butter. The international application WO 2014/174113 A2 particularly discloses a hair dyeing composition comprising natural dyes, an oil and a saccharide. These compositions may show limited dustiness and may provide satisfactory dyeing results. However, the presence of oil may negatively impact the miscibility of the hair dyeing composition with water, even with warm water, thereby complicating the mixing and the application onto hair. In addition, the presence of oil may leave residues on hair, leaving it greasy even after rinsing-off the poultice, requiring excessive use of shampoo thereby impairing the hair feel and potentially weakening the colour result.

There is thus still the need for providing a dust-free non-oxidative hair dyeing composition, that could be easily mixed with water before application onto hair. There is also the need for providing a non-oxidative hair dyeing composition mostly comprising natural compounds, particularly compounds of plant origin, without compromising the dyeing performance. There is also the need for providing a simple non-oxidative hair dyeing composition i.e. a composition with fewer compounds as usual, without compromising the dyeing performance. There is the need for providing a flowable non-oxidative hair dyeing composition, which could be applied onto hair as a poultice, after mixing with water, with limited or no dripping. There is also the need for providing a hair dye composition providing an improved user's dyeing experience and an even dyeing of hair, without comprising shine and hair feel. There is also the need for providing a hair dye composition with improved shine and hair feel.

SUMMARY

In a first aspect, the present invention relates to a granulated hair dyeing composition comprising at least 60% of a natural hair dyeing agent, from 10 to 30% of a natural thickening agent, and optionally from 0 to 10% of a direct dye, by total weight of the composition, wherein the natural dyeing agent is coated with the natural thickening agent, thereby forming granules.

In some embodiments, the granulated hair dyeing composition is substantially anhydrous.

In some embodiments, the granulated hair dyeing composition is obtained by fluid bed granulation.

In some embodiments, the natural dyeing agent is selected from the group consisting of Lawsonia Inermis leaf powder (henna), a powder of an indigo-yielding plant, and their mixtures; preferably from the group consisting of Lawsonia Inermis leaf powder (henna), a powder of an indigo-yielding plant and their mixtures.

In some embodiments, the natural thickening agents is selected from the group consisting of glucans, modified and unmodified polysaccharides, amylose, amylopectin, glycogen, dextrans, celluloses and derivatives thereof, mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, xanthan gums, gellan gums, welan gums, scleroglucans, succinoglycans, and mixtures thereof preferably from the group consisting of maltodextrin, xantham gum, Cyamopsis Tetragonoloba (Guar) gum, and mixtures thereof.

In some embodiments, the direct dyes, if present, are selected from the group consisting of HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Red 76, Basic Violet 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, 4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, hydroxyethyl-2-nitro-p-toluidine, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Blue No. 2, HC Blue No. 16, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14 and mixtures thereof.

In some embodiments, the granulated hair dyeing composition further comprises a natural conditioning agent; preferably a natural conditioning agent may be selected from the group consisting of Cassia Auriculata leaf powder, Cassia Angustifolia leaf powder, and their mixtures.

In some embodiments, the granulated hair dyeing composition is substantially free of any fatty compound; preferably it is substantially free of any fatty compound selected from the group consisting of mineral fatty compounds, fatty compounds of plant origin, animal fatty compounds, synthetic fatty compounds, and mixtures thereof.

In some embodiments, the granulated hair dyeing composition is substantially free of any surfactant; preferably from any surfactant selected from the group consisting of anionic surfactant, cationic surfactant, nonionic surfactant, amphoretic surfactant and mixtures thereof.

In some embodiments, the granulated hair dyeing composition is a non-oxidative composition; preferably it is a non-oxidative composition being substantially free of an oxidative dye precursor, an oxidizing agent, an alkalizing agent, a reducing agent and mixtures thereof.

In a second aspect, the present invention relates to a method for obtaining the granulated hair dyeing composition, as described herein, comprising the following steps:
  providing a powder comprising a natural hair dyeing agent;
  providing an aqueous solution of a natural thickening agent;
  moistening the powder with the aqueous solution of the natural thickening agent in order to obtain granules; and
  drying the granules.

In a third aspect, the present invention relates to a hair dyeing poultice comprising the hair dyeing composition as described herein and a cosmetically acceptable aqueous carrier, wherein the hair dyeing composition and the cosmetically acceptable aqueous carrier are mixed in a weight ratio from 1:1 to 1:10, preferably from 1:2 to 1:7, more preferably from 1:3 to 1:5.

In a fourth aspect, the present invention relates to a method for dyeing hair, comprising the following steps:
  providing of a granulated hair dyeing composition as described herein;
  mixing homogeneously the hair dyeing composition with a cosmetically acceptable carrier, preferably with water, more preferably with warm water, in a weight ratio of 1:5;
  applying the homogenous hair dyeing poultice onto hair;
  allowing the applied hair dyeing poultice to act on the hair for a predetermined acting time;
  rinsing the hair with water;
  optionally washing the hair with shampoo;
  optionally rinsing with water; and
  optionally blow-drying the hair until it is 90% dry.

In a fifth aspect, the present invention relates to a method of use of the granulated hair dyeing composition, and the hair dyeing poultice obtained from it, for the semi-permanent dyeing of hair.

The inventors have shown that a granulated non-oxidative hair dyeing composition, while having a "simple" formulation and mostly—or exclusively—comprising natural compounds, particularly compounds of plant origin, still provides a satisfactory user's experience both in terms of mixing with water, application onto hair as a poultice, dyeing results, shine and hair feel. Particularly, the granulated non-oxidative hair dyeing compositions is dust-free, even though it is substantially free of any fatty compound. It is also a flowable composition, which could be applied onto hair as a poultice, after mixing with water, however with limited or no dripping. The inventors have shown that the granules forming the hair dyeing composition, particularly when obtained using a fluid bed granulation method, allow providing the properties and advantages listed herein.

DETAILED DESCRIPTION

As used herein the term "hair" may be "living", i.e., on a living body, or may be "non-living", i.e., in a wig, hairpiece or other aggregation of non-living keratinous fibers. Mammalian, preferably human hair is preferred. However wool, fur and other keratin containing fibers are suitable substrates for the compositions according to the present invention.

By "at least one compound" or "a compound" is meant one compound or a mixture of two or more compounds belonging to the defined class of said compounds.

By "natural" is meant that the respective compound is produced by or results from the activity of a living organism, and excludes compounds derived from fossil resources. In particular, the term "natural" denotes compounds derived from a (living) plant, and implies that the respective compound generally is bio-degradable.

By "substantially anhydrous" is meant a composition comprising 1% or less, preferable 0.1% or less, more preferably about 0% water, by total weight of the composition.

By "substantially free of" is meant a composition comprising 1% or less, preferable 0.5% or less, more preferably 0.1% or less, such as for example 0.01% or less of the respective compound, by total weight of the composition.

By "room temperature" is meant a temperature of about 25° C.

By "atmospheric pressure" is meant a pressure of about 760 mmHg.

By "dust-free" is meant a composition comprising 5% or less, preferable 2% or less, more preferably 1% or less, by total weight of the composition, of powders with particle sizes of less than 50 μm, measured using sieve analysis.

All percentages are by weight of the granulated hair dyeing composition, i.e. of the composition before mixing with water, unless otherwise specified. Also, ratios are weight ratios unless specifically stated otherwise.

Granulated Hair Dyeing Composition

In a first aspect, the present invention relates to a granulated hair dyeing composition comprising at least 60% of a natural dyeing agent, from 10 to 30% of a natural thickening agent, and optionally from 0 to 10% of a direct dye, by total weight of the composition, wherein the natural dyeing agent is coated with the natural thickening agent, thereby forming granules. The composition is anon-oxidative hair dyeing composition (i.e. it is not an oxidative hair dyeing composition).

By "granulated hair dyeing composition" is meant a composition formed of granules. The granules are formed by the natural dyeing agents, optionally the direct dyes and any other compounds, which are coated by the natural thickening agents. The granules may be obtained using any suitable granulation process, particularly by using fluid bed granulation.

In one embodiment, the granulated hair dyeing composition is obtained by fluid bed granulation.

The granules are irregularly shaped with specific surface area between 0.4 m$^2$/g to 0.7 m$^2$/g, preferably from 0.45 m$^2$/g to 0.65 m$^2$/g. The specific surface area is measured using the Gas Adsorption BET-Method.

The granules have an average size from 710 to 1000 μm. The average size is measured using sieve analysis. The size of the granules is distributed from 100 μm to 1000 μm.

The granules have a density from 1.2 to 1.5 g/cm$^3$, preferably from 1.25 to 1.45 g/cm$^3$. The density is measured using Gas-Pycnometer Ultrapyc 5000. Each sample was measured at least 25 times and the mean value was calculated from the measurements.

The granules have a cohesive strength from 60 to 120 Pa, preferably from 65 to 115 Pa. The cohesive strength of the granules is measured using MCR 302 Powder cell rheometer.

In one embodiment, the hair dyeing composition is substantially anhydrous.

In one embodiment, the hair dyeing composition is compact.

Natural Dyeing Agents

The composition comprises at least one natural dyeing agent. The natural dyeing agent is selected from the group consisting of *Lawsonia Inermis* leaf powder (henna), a powder of an indigo-yielding plant and their mixtures. The composition may also comprise an additional natural dyeing agent selected from the group consisting of chamomile flowers, *curcuma* roots, rhubarb, buckthorn bark, olive tree leaves, Canadian bloodroot, turmeric, yellowwood, redwood, logwood, madder root, black elderberry, black chokeberry and mixtures thereof.

The indigo-yielding plant may be chosen from the genera *Indigofera* (e.g. *Indigofera tinctoria, Indigofera suffraticosa, Indigofera articulata, Indigofera arrecta, Indigofera geradiana, Indigofera argenta, Indigofera indica, Indigofera* longiracemosa and mixtures thereof), *Isatis* (e.g. *Isatis tinctoria*), *Polygonum* or *Persicaria* (e.g. *Polygonum tinctorium* or *Persicaria tinctoria*), *Wrightia* (e.g. *Wrightia tinctoria*), *Calanthe* (e.g. *Calanthe veratrifolia*), *Baphicacanthus* (e.g. *Basphicacanthus cusia*) and mixtures thereof; preferably the indigo-yielding plant is chosen from the genera *Indigofera*; more preferably the indigo-yielding plant is *Indigofera tinctoria*.

In one embodiment, the composition comprises a natural dyeing agent consisting of *Lawsonia Inermis* leaf powder (free of a powder of an indigo-yielding plant). In another embodiment, the composition comprises a natural dyeing agent consisting of a powder of an indigo-yielding plant (free of *Lawsonia Inermis* leaf powder). In another embodiment, the composition comprises a natural dyeing agent being a mixture of *Lawsonia Inermis* leaf powder and a powder of an indigo-yielding plant. In another embodiment, the composition comprises a natural dyeing agent being a mixture of *Lawsonia Inermis* leaf powder, a powder of an indigo-yielding plant and a powder of an additional natural dyeing agent selected from the group consisting of chamomile flowers, *curcuma* roots, rhubarb, buckthorn bark, olive tree leaves, Canadian bloodroot, turmeric, yellowwood, redwood, logwood, madder root, black elderberry, black chokeberry and mixtures thereof.

The composition comprises at least 60%, preferably from 60 to 90%, more preferably from 60 to 85%, most preferably from 65 to 80%, of the natural dyeing agent, by total weight of the composition.

If present, the composition may comprise from 0.1 to 90%, preferably from 0.5 to 85%, more preferably from 1 to 80%, of *Lawsonia Inermis* leaf powder, by total weight of the composition. In some embodiment, the composition may comprise from 0.1 to 5%, or from 5 to 10%, or from 10 to 15%, or from 15 to 20%, or from 20 to 25%, or from 25 to 30%, or from 30 to 35%, or from 35 to 40%, or from 40 to 45%, or from 45 to 50%, or from 50 to 55%, or from 55 to 60%, or from 60 to 65%, or from 65 to 70%, or from 70 to 75%, or from 75 to 80%, or from 80 to 85%, or from 85 to 90%, of *Lawsonia Inermis* leaf powder, by total weight of the composition.

If present, the composition may comprise from 0.1 to 90%, preferably from 0.5 to 85%, more preferably from 1 to 80%, of a powder of an indigo-yielding plant, by total weight of the composition. In some embodiment, the composition may comprise from 0.1 to 5%, or from 5 to 10%, or from 10 to 15%, or from 15 to 20%, or from 20 to 25%, or from 25 to 30%, or from 30 to 35%, or from 35 to 40%, or from 40 to 45%, or from 45 to 50%, or from 50 to 55%, or from 55 to 60%, or from 60 to 65%, or from 65 to 70%, or from 70 to 75%, or from 75 to 80%, or from 80 to 85%, or from 85 to 90%, of a powder of an indigo-yielding plant, by total weight of the composition.

If present, the composition may comprise from 0.1 to 90%, preferably from 0.5 to 85%, more preferably from 1 to 80%, of an additional natural dyeing agent, by total weight of the composition. In some embodiment, the composition may comprise from 0.1 to 5%, or from 5 to 10%, or from 10 to 15%, or from 15 to 20%, or from 20 to 25%, or from 25 to 30%, or from 30 to 35%, or from 35 to 40%, or from 40 to 45%, or from 45 to 50%, or from 50 to 55%, or from 55 to 60%, or from 60 to 65%, or from 65 to 70%, or from 70 to 75%, or from to 80%, or from 80 to 85%, or from 85 to 90%, of a powder of an additional natural dyeing agent, by total weight of the composition.

Natural Thickening Agents

The composition also comprises at least one natural thickening agent.

The natural thickening agents may be selected from the group consisting of glucans, modified and unmodified polysaccharides (such as those derived, for example, from cereals, for instance wheat, corn or rice, from vegetables, for instance yellow pea, and tubers, for instance potato or cassaya; maltodextrin), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans (such as guar gums hydroxypropyl guar gum), xanthan gums, gellan gums, welan gums, scleroglucans, succinoglycans, and mixtures thereof; preferably from the group consisting of maltodextrin, xanthan gum, *Cyamopsis Tetragonoloba* (Guar) gum and mixtures thereof. Suitable natural thickening agents are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., all three being incorporated herein by reference.

The natural thickening agent is sprayed onto the hair dyeing agent in order to obtain granules as described herein. Any suitable granulation method may be used, particularly the fluid bed granulation method.

The composition comprises from 10 to 30%, preferably from 15 to 27%, more preferably from 20 to 25%, of the natural thickening agent, by total weight of the composition.

Direct Dyes

The composition may also comprise at least one direct dye. The addition of direct dyes may prevent off-tones from natural dyes, which usually need some time e.g. 48 h to develop to their final color, and/or may also increase the color space that can be achieved versus compositions only comprising natural dyes.

The direct dyes may be selected from the group consisting of HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Red 76, Basic Violet 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methyl sulfate, (E)-1-(2-(4-(4,5-dimethylthiazol-2-yl) diazenyl)phenyl)(ethyl)amino)ethyl)-3-methyl-1H-imidazol-3-ium chloride, (E)-4-(2-(4-(dimethylamino) phenyl)diazenyl)-1-methy 1-1H-imidazol-3-ium-3-yl) butane-1-sulfonate, (E)-4-(4-(2-methyl-2-phenylhydrazono) methyl)pyridinium-1-yl)butane-1-sulfonate, N,N-di methyl-3-(4-(methyl amino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methyl amino)-4-nitrophenoxy) ethanol, 3-(3-amino-4-nitrophenyl)propane-1,2-diol, hydroxyethyl-2-nitro-p-toluidine, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Blue No. 2, HC Blue No. 16, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14 and mixtures thereof.

If present, the composition may comprise from 0.1 to 10%, preferably from 0.5 to 9%, more preferably from 1 to 8.5%, of the direct dye, by total weight of the composition.

Alternatively, the hair dyeing composition may be substantially free of any additional direct dyes.

Natural Conditioning Agent

The composition may also comprise at least one natural conditioning agent. The addition of a natural conditioning agent will bring increased shine. Furthermore, hair treated with the natural hair dye composition feels stronger and more voluminous.

The natural conditioning agent may be selected from the group consisting of *Cassia Auriculata* leaf powder, *Cassia Angustifolia* leaf powder, and their mixtures.

In one embodiment, the composition comprises a natural conditioning agent consisting of *Cassia Auriculata* leaf powder, *Cassia Angustifolia* leaf powder, and their mixtures.

If present, the composition may comprise from 0.1 to 90%, preferably from 0.5 to 85%, more preferably from 1 to 80%, of the natural conditioning agent, by total weight of the composition.

Fatty Compounds

The composition may be substantially free of any fatty compound. "Fatty compounds" means compounds that are insoluble in water at room temperature and at atmospheric pressure i.e. a compound having a solubility of less than 5%, preferably less than 1%, more preferably less than 0.1%, in water. Fatty compounds are also generally soluble in organic solvents (e.g. chloroform, dichloromethane, carbon tetrachloride, ethanol, benzene, toluene, tetrahydrofuran, liquid petrolatum jelly or decamethylcyclopentasiloxane) under the same temperature and pressure conditions. They comprise in their structure at least one hydrocarbon chain comprising at least 6 carbon atoms or a sequence of at least two siloxane groups.

The fatty compound may be selected from the group consisting of mineral fatty compounds, fatty compounds of plant origin, animal fatty compounds, synthetic fatty compounds, and mixtures thereof.

The fatty compounds may be selected from the group consisting of non-silicone fatty compounds, silicone fatty compounds and mixtures thereof.

The fatty compounds may be liquid or solid at room temperature and at atmospheric pressure.

The fatty compound may be a non-silicone oil. "Oil" means a fatty compound that is liquid at room temperature and at atmospheric pressure. Examples of natural oils include, but are not limited to, jojoba oil, babassu oil, sunflower oil, olive oil, coconut oil, Brazil nut oil, marula oil, corn oil, argan oil, soybean oil, grapeseed oil, flax oil, sesame oil, hazelnut oil, apricot oil, *macadamia* oil, arara oil, castor oil, avocado oil, shea butter oil, rapeseed oil, rice bran oil, almond oil and mixtures thereof.

Examples of synthetic oils include, but are not limited to, alkanes of C6-016, esters of fatty acids and/or alcohols, fatty alcohols, paraffin oils, and mineral oil.

The fatty compound may be a non-silicone butter. "Butter" means a lipophilic fatty compound which undergoes a reversible solid/liquid change of state and which comprises, at room temperature and at atmospheric pressure, a liquid fraction and a solid fraction. Examples of butters include, but are not limited to, shea butter, Karite Nilotica butter (*Butyrospermum parkii*), galam butter, (*Butyrospermum parkii*), Borneo butter or fat or tengkawang tallow (*Shorea stenoptera*), shorea butter, illipe butter, *madhuca* butter or *Bassia madhuca longifolia* butter, mowrah butter (*Madhuca latifolia*), katiau butter (*Madhuca mottleyana*), phulwara butter (*M. butyracea*), manga butter (*Mangifera indica*), murumuru butter (Astrocaryum murumuru), koku m butter (*Garcinia indica*), ucuuba butter (*Virola sebifera*), tucuma butter, painya butter (Kpang nan) (*Pentadesma butyracea*), coffee butter (*Coffea arabica*), apricot butter (*Prunus armeniaca*), macadamia butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*), cacao butter, sunflower butter and mixtures thereof.

The fatty compound may be a non-silicone wax. "Wax" means a fatty compound that is solid at room temperature and at atmospheric pressure. The wax may be selected from the group consisting of fatty alcohols, fatty esters, waxes of plant origin, animal waxes, marine waxes and mixtures thereof. Examples of waxes include, but are not limited to, carnauba wax, candelilla wax, esparto wax, paraffin wax, ozokerite, olive tree wax, rice wax, hydrogenated jojoba wax, absolute flower waxes, beeswaxes, modified beeswaxes (cerabellina), polyethylene waxes or polyolefin waxes.

The fatty compound may a silicone fatty compound, such as a silicone wax, a silicone resin, a silicone gum and mixtures thereof. Examples of silicone fatty compounds include, but are not limited to, polydialkylsiloxane (such polydimethylsiloxane), dimethicone, dimethiconol, organopolysiloxane.

Surfactant

The composition may be substantially free of a surfactant. "Surfactant" usually means a compound having a lipophilic chain length of from about 8 to about 30 carbon atoms.

The surfactant may be selected from the group consisting of anionic surfactant, cationic surfactant, nonionic surfactant, amphoretic surfactant and mixtures thereof.

Examples of anionic surfactants include, but are not limited to salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Examples of non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$) alkylamine oxides or N-acylaminopropylmorpholine oxides.

Examples of amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CON $HCH_2CH_2$—$N^+(R_3)(R_4)(CH_2COO^-)$, (XIX) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—$CONHCH_2CH_2$—N(B)(C) (XX) wherein B represents —$CH_2CH_2OX'$, C represents —$(CH_2)_z$—Y', with z=1 or 2, X' is chosen from the —$CH_2CH_2$—COOH group and a hydrogen atom, Y' is chosen from —COOH and —$CH_2$—CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium caryloamphodiacetate, disodium cocoamphodipropionate, disodium lauroamphodipropionate, disodium caprylamphodipropionate, disodium caryloamphodipropionate, lauroamphodipropionic acid, and cocoamphodipropionic acid. Salts of diethyl aminopropyl cocoaspartamid can be also used.

Examples of cationic surfactants include, but are not limited to, the quaternary ammonium salts A) to D) as defined hereinafter:

A) Quaternary ammonium salts of general formula (IX) below:

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from ($C_{12}$-$C_{22}$)alkylamido($C_2$-$C_6$)alkyl and ($C_{12}$-$C_{22}$) alkylacetate radicals. A suitable cationic surfactant is, for example, a dicetyldimethyl ammonium salt (for example chloride);

B) Quaternary ammonium salts of imidazolinium of formula (XI) below:

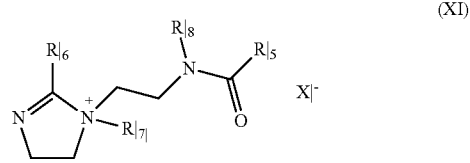

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (XII):

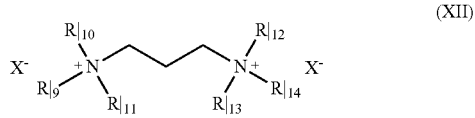

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallow-diammonium dichloride.

D) Quaternary ammonium salts comprising at least one ester function, of formula (XIII) below:

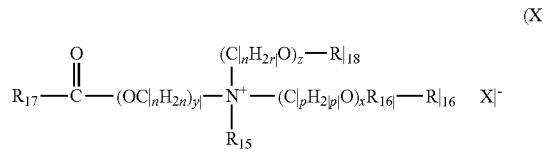

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X− is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XXXXI) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Oxidative Dye Precursor

The granulated hair dyeing composition may be substantially free of an oxidative dye precursor. Oxidative dye precursor are usually classified either as primary intermediates (also known as developers) or couplers (also known as secondary intermediates).

Examples of primary intermediates include, but are not limited to: toluene-2,5-diamine, p-phenylenediamine, N-phenyl-p-phenylene di amine, N,N-bis(2-hydroxyethyl)-p-phenylenediamine, 2-hydroxyethyl-p-phenylenedi amine, hydroxypropyl-bis-(N-hydroxyethyl-p-phenylenedi amine), 2-methoxymethyl-p-phenylenedi amine, 2-(1,2-dihydroxyethyl)-p-phenylenedi amine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, (2,3-diamino-6,7-dihydro-1H,5H-pyrazolo[1,2-a]pyrazol-1-one dimethanesulfonate), 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy] ethanol hydrochloride, salts thereof and mixtures thereof.

Examples of couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethyl aminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene) bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5 (4H)-one, 1,2,4-trihydroxybenzene, 2-(benzo[d][1,3]dioxol-5-ylamino)ethanol (also known as hydroxyethyl-3,4-methylenedioxy aniline), and mixtures thereof.

Oxidizing Agent

The granulated hair dyeing composition may be substantially free of an oxidizing agent (or a source of an oxidizing agent), such as water-soluble peroxygen oxidizing agents. Examples of water-soluble peroxygen oxidizing agents include, but are not limited to: hydrogen peroxide, inorganic alkali metal peroxides (such as sodium periodate and sodium peroxide), organic peroxides (such as urea peroxide and melamine peroxide), inorganic perhydrate salt bleaching compounds (such as the alkali metal salts of perborates, percarbonates, perphosphates, persilicates, persulfates and the like), alkyl and aryl peroxides, peroxidases, oxidases, uricases, a source of peroxymonocarbonate ions formed in situ from a source of hydrogen peroxide and a hydrogen carbonate ion source, a source of ammonia or ammonium ions.

Alkalizing Agent

The granulated hair dyeing composition may be substantially free of any alkalizing agent. Examples of alkalizing agents include, but are not limited to: as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. In an embodiment, the alkalizing agent may be ammonia and/or monoethanolamine.

Reducing Agent

The granulated hair dyeing composition may be substantially free of any reducing agent. The reducing agents usually comprise a mercapto-functional group. Examples of reducing agents include, but are not limited to: thioglycolic acid, thiolactic acid and their salts thereof, such as their ammonium and ethanolamine salts; cysteine and its salts thereof, such as hydrochloride cysteine; homocysteine; cysteamine and its salts thereof; N-acetyl cysteine; thioglycerol; ethanediol monothioglycolate; 1,2-propyleneglycol monothioglycolate; 1,3-propanediol monothioglycolate or the isomer mixture resulting therefrom; 1,3-butanediol, 1,4-butanediol monothioglycolate and their isomer mixtures therefrom; polyethylene glycol monothioglycolates, such as di-, tri- and tetraethyleneglycol monothioglycolates; glycerol monothiolactate; mercapto carboxylic acids and esters thereof; N-alkyl-2-mercaptoacetamides; and mixtures thereof.

Solvent

The granulated hair dyeing composition may be substantially free of any solvent. Examples of solvent include, but are not limited to: water, or a mixture of water and at least one organic solvent to dissolve the compounds that would not typically be sufficiently soluble in water. Examples of organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

Chelants

The granulated hair dyeing composition may be substantially free of any chelant (also known as "chelating agent", "sequestering agent", or "sequestrant"). Examples of chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof alternatively monoethanolammonium salts, diethanolammonium salts, triethanolammonium salts, and mixtures thereof.

Radical Scavengers

The granulated hair dyeing composition may be substantially free of any radical scavenger. Examples of radical scavengers include, but are not limited to: alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methyl pyrazol-5-one-3-carboxylate, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methyl propan-1-ol, 1-amino-2-methyl propan-2-ol, 3-aminopropane-1,2-diol, glucosamine, N-acetylglucosamine, glycine, arginine, lysine, proline, glutamine, histidine, sarcosine, serine, glutamic acid, tryptophan, or mixtures thereof, or the salts, such as the potassium, sodium, or ammonium salts thereof, or mixtures thereof.

Fragrances

The granulated hair dyeing composition may be substantially free of any fragrances.

Method for Obtaining the Granulated Hair Dyeing Composition

In a second aspect, the present invention relates to a method for obtaining the granulated hair dyeing composition comprising the following steps:

providing a powder comprising a natural hair dyeing agent;

providing an aqueous solution of a natural thickening agent;

moistening the powder with the aqueous solution of the natural thickening agent in order to obtain granules; and drying the granules.

The moistening of the powder with the aqueous solution helps form liquid bridges.

The drying of the granules helps stabilizing the granules through the binder. The drying step may be implemented at low mechanical compression.

When present, in one embodiment, the direct dye may be provided together with the natural hair dyeing agent as a powder, prior moistening with the aqueous solution. In another embodiment, the direct dye may be added after moistening the powder with the aqueous solution.

The method may be implemented using fluid bed agglomeration.

This method is particularly suitable for obtaining the granulated hair dyeing compositions according to the present invention, as it allows obtaining granules as above-described i.e. granules comprising core materials (such as the natural dyeing agents, the natural conditioning agents and the optional direct dyes) coated with natural thickening agents.

Hair Dyeing Poultice

In a third aspect, the present invention relates to a hair dyeing poultice comprising the hair dyeing composition and a cosmetically acceptable aqueous carrier, wherein the hair dyeing composition and the cosmetically acceptable aqueous carrier are mixed in a weight ratio from 1:1 to 1:10, preferably from 1:2 to 1:7, more preferably from 1:3 to 1:5. The hair dyeing poultice is a ready-to-use formulation, which can be applied onto hair.

The cosmetically acceptable aqueous carrier comprises water, preferably consists of (is) water. In one embodiment, the cosmetically acceptable aqueous carrier (and thus the granulated hair dyeing composition) is substantially free of water-soluble polyhydric alcohols.

The granulated hair dyeing composition may be mixed with a cosmetically acceptable aqueous carrier having a temperature from 20 to 90° C., preferably from 40 to 85° C., more preferably from 60 to 80° C.

The hair dyeing poultice may have a rheological profile with the complex modulus G* from about 30 to about 60 and a tan delta from about 0.80 to about 1.00.

Method for Dyeing Hair

In a fourth aspect, the present invention relates to a method for dyeing hair, comprising the following steps:
  providing of a granulated hair dyeing composition;
  mixing homogeneously the hair dyeing composition with a cosmetically acceptable carrier, preferably with water, more preferably with warm water, in a weight ratio from 1:7 to 1:3, preferably from 1:6 to 1:4, more preferably of about 1:5;
  applying the homogenous hair dyeing poultice onto hair;
  allowing the applied hair dyeing poultice to act on the hair for a predetermined acting time, preferably from about 5 to about 60 min;
  rinsing the hair with water;
  optionally washing the hair with shampoo;
  optionally rinsing the hair with water; and
  optionally blow-drying the hair until it is 90% dry.

Method of Use

In a fifth aspect, the present invention relates to a method of use of the granulated hair dyeing composition, and the hair dyeing poultice obtained from it, for the semi-permanent dyeing of hair.

EXAMPLES

Preparation of the Granulated Hair Dyeing Composition (Invention)

A fluid-bed, wet-granulation process consists of dry blending, wet granulation, and drying. The fluid bed granulation process (also known as agglomeration) involves suspending particles in an air stream and spraying a binder liquid from the top of the system down onto the fluidized bed (top-down spray). Particles in the path of the spray are moistened and agglomerate. During drying the particles are stabilised through the binder used. By control of spray and air flow rates particle size distribution and particle stability are controlled.

Hair Dyeing Compositions

Depending on the desired range, the proportion in natural hair dyeing agent, in direct dye and in natural thickening agent may vary.

| Materials (weight percent) | C1 | C2 |
|---|---|---|
| *Lawsonia inermis* leaf powder | 1-80.4 | 1-80.4 |
| *Indigofera tinctoria* leaf powder | 0-74.9 | 0-74.9 |
| *Cassia Auriculata* leaf powder | 0-78.5 | 0-78.5 |

-continued

| Materials (weight percent) | C1 | C2 |
|---|---|---|
| Direct dyes | 0.01-5.2 | 0.01-5.2 |
| Guar gum | 6.0 | — |
| Xantham gum | — | 4.5 |
| Maltodextrin | 19 | 19 |
| Total of materials | 100.0 | 100.0 |

As shown below, granulated hair dyeing compositions for providing blonde shades may predominantly comprise *Cassia Auriculata* leaf powder; granulated hair dyeing compositions for providing blonde shades may predominantly comprise *Lawsonia inermis* leaf powder; *Indigofera tinctoria* leaf powder.

| Materials (weight percent) | Blonde | Red | Brown |
|---|---|---|---|
| *Lawsonia inermis* leaf powder | 4.5 | 74.9 | 14.5 |
| *Indigofera tinctoria* leaf powder | — | — | 45.5 |
| *Cassia Auriculata* leaf powder | 70.0 | — | 6.0 |
| Direct dyes | 0.5 | 0.1 | 9.0 |
| Guar gum | 6.0 | 6.0 | 6.0 |
| Maltodextrin | 19 | 19 | 19 |
| Total of materials | 100.0 | 100.0 | 100.0 |

Hair Dyeing Poultice

| Materials (weight percent) | C2 | C3 |
|---|---|---|
| Hair dyeing composition | 20 | 20 |
| Cosmetically acceptable carrier | 80 (q.s. 100) | 80 (q.s. 100) |

Hair Dyeing Method

The hair dyeing method is conducted as follows:
  providing of a granulated hair dyeing composition;
  mixing homogeneously the hair dyeing composition with water (at a temperature of 70° C.) in a weight ratio of 1:5;
  applying the homogenous hair dyeing mixture on hair;
  allowing the applied hair dyeing mixture to act on the hair for a predetermined acting time from 5 to 60 min;
  rinsing the hair with water;
  optionally washing the hair with shampoo;
  optionally rinsing with water; and
  optionally blow-drying the hair until it is 90% dry.

Results

| Criteria | C2 | C3 |
|---|---|---|
| Cohesive strength (Pa) | 68 | 64 |

Variations and modifications of the invention and further embodiments thereof, in addition to those described herein, will become apparent to those skilled in the art from the full contents of this document. The subject matter herein contains information, exemplification and guidance that can be adapted to the practice of this invention in its various embodiments and equivalents thereof. It is intended that the appended claims cover all such variations, modifications, embodiments and equivalents.

The invention claimed is:

1. An anhydrous granulated hair dyeing composition comprising at least 60% by weight of a natural hair dyeing agent, from 10 to 30% by weight of a natural thickening agent, and optionally from 0 to 10% by weight of a direct dye, by total weight of the composition;
   wherein the natural dyeing agent is coated with the natural thickening agent, thereby forming granules;
   wherein the natural dyeing agent is selected from the group consisting of *Lawsonia Inermis* leaf powder (henna), a powder of an indigo-yielding plant, and their mixtures;
   wherein the natural thickening agent is selected from the group consisting of maltodextrin, xanthan gum, *Cyamopsis Tetragonoloba* (Guar) gum and mixtures thereof; wherein the granulated hair dyeing composition is obtained by a method consisting of the following steps:
   providing a powder comprising the natural hair dyeing agent;
   providing an aqueous solution of the natural thickening agent;
   moistening the powder with the aqueous solution of the natural thickening agent in order to obtain granules; and -drying the granules.

2. The anhydrous granulated hair dyeing composition according to claim 1, wherein the natural thickening agent is a mixture of maltodextrin and xanthan gum, or a mixture of maltodextrin and *Cyamopsis Tetragonoloba* (Guar) gum.

3. The anhydrous granulated hair dyeing composition according to claim 1, wherein it is obtained by fluid bed granulation.

4. The anhydrous granulated hair dyeing composition according to claim 1, wherein the direct dyes are selected from the group consisting of HC Yellow 17, HC Blue 18, HC Yellow 16, HC Red 18, Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Red 76, Basic Violet 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)4-methylmorpholin-4-ium-methylsulfate, (E)-1-(2-(4-(4,5-dimethylthiazol-2yl)diazenyl)phenyl) (ethyl)amino)ethyl)-3-methyl-1H-imidazol-3-ium chloride, (E)-4-(2 (4-(dimethylamino)phenyl)diazenyl)-1-methyl-1H-imidazol-3-ium-3-yl)butane-1 sulfonate, (E)-4-(4-(2-methyl-2-phenylhydrazono)methyl)pyridinium-1-yl)butane-1 sulfonate, N,N-dimethyl-3-(4-(methylamino)-9,10-dioxo-4a,9,9a, 10-tetrahydroanthracen 1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3nitrophenol, 2-(3-(methylamino)-4-nitrophenoxy)ethanol, 3-(3-amino-4-nitrophenyl) propane-1,2-diol, hydroxyethyl-2-nitro-p-toluidine, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Blue No. 2, HC Blue No. 16, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6nitropyridine-2,5-diamine, HC Violet No. 2, 2-amino-6-chloro-4-nitrophenol, 4-(3hydroxypropylamino)-3-nitrophenol, HC Yellow No. 13, 6-nitro-1,2,3, 4tetrahydroquinoxaline, HC Red No. 14, HC Yellow No. 15, HC Yellow No. 14, N2-methyl6-nitropyridine-2,5-diamine, N1-allyl-2-nitrobenzene-1,4-diamine, HC Red No. 8, HC Green No. 1, HC Blue No. 14 and mixtures thereof.

5. The anhydrous granulated hair dyeing composition according to claim 1, further comprising a natural conditioning agent.

6. The anhydrous granulated hair dyeing composition according to claim 1, wherein it is free of any fatty compound.

7. The anhydrous granulated hair dyeing composition according claim 1, wherein it is free of any surfactant.

8. The anhydrous granulated hair dyeing composition according to claim 1, wherein it is a non-oxidative composition.

9. A method for obtaining an anhydrous granulated hair dyeing composition comprising at least 60% by weight of a natural hair dyeing agent, from 10 to 30% by weight of a natural thickening agent, and optionally from 0 to 10% by weight of a direct dye, by total weight of the composition, wherein the natural dyeing agent is coated with the natural thickening agent, thereby forming granules, the method consisting of the following steps:
   providing a powder comprising the natural hair dyeing agent, wherein the natural dyeing agent is selected from the group consisting of *Lawsonia Inermis* leaf powder (henna), a powder of an indigo-yielding plant, and their mixtures;
   providing an aqueous solution of the natural thickening agent, wherein the natural thickening agent is selected from the group consisting of maltodextrin, xanthan gum, *Cyamopsis Tetragonoloba* (Guar) gum and mixtures thereof;
   moistening the powder with the aqueous solution of the natural thickening agent in order to obtain granules; and—drying the granules.

10. A hair dyeing poultice comprising the hair dyeing composition according to claim 1 and a cosmetically acceptable aqueous carrier, wherein the hair dyeing composition and the cosmetically acceptable aqueous carrier are mixed in a weight ratio from 1:1 to 1:10.

11. A method for dyeing hair, comprising the following steps:
   providing of a granulated hair dyeing composition according to claim 1;
   mixing homogeneously the hair dyeing composition with a cosmetically acceptable carrier in a weight ratio of 1:5;
   applying the homogenous hair dyeing poultice onto hair;
   allowing the applied hair dyeing poultice to act on the hair for a predetermined acting time;
   rinsing the hair with water;
   optionally washing the hair with shampoo;
   optionally rinsing with water; and
   optionally blow-drying the hair until it is 90% dry.

12. The anhydrous granulated hair dyeing composition according to claim 5, wherein the natural conditioning agent is selected from the group consisting of *Cassia Auriculata* leaf powder, *Cassia Angustifolia* leaf powder, and their mixtures.

\* \* \* \* \*